(12) United States Patent
Suri et al.

(10) Patent No.: US 6,455,035 B1
(45) Date of Patent: Sep. 24, 2002

(54) ANGIOPOIETINS AND METHODS OF USE THEREOF

(75) Inventors: Chitra Suri, Tarrytown, NY (US); Gavin Thurston, San Francisco, CA (US); Donald Mc Donald, San Francisco, CA (US); George D. Yancopoulos, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 09/286,033

(22) Filed: Apr. 5, 1999

Related U.S. Application Data

(60) Provisional application No. 60/106,539, filed on Mar. 26, 1999.

(51) Int. Cl.[7] .......................... A61K 38/18; A61K 38/19
(52) U.S. Cl. .......................... 424/85.1; 514/2; 514/8; 514/12; 514/885
(58) Field of Search .......................... 514/2, 8, 12, 885; 424/85.1

(56) References Cited

FOREIGN PATENT DOCUMENTS

| WO | WO 96/11269 | 4/1996 |
|----|-------------|--------|
| WO | WO 96/31598 | 10/1996 |
| WO | WO 98/05779 | 2/1998 |

OTHER PUBLICATIONS

AM. J. Physiol., vol. 266, issued 1994, Baluk, P. and McDonald, D.M., "The β2–adrenergic receptor agonist formoterol reduces microvascular leakage by inhibiting endothelial gap formation", pp. L461–468.

Am. J. Pathol., vol. 152, No. 6, issued Jun. 1998, Baluk, P., et al., "Endothelial Gaps and Adherent Leukocytes in Allergen–Induced Early–and Late–Phase Plasma Leakage in Rat Airways", pp. 1463–1476.

J. Pharmacol. Exp. Ther., vol. 284, No. 2, issued 1998, Baluk, P., et al., "Anti–inflammatory Mystixin Peptides Inhibit Plasma Leakage Without Blocking Endothelial Gap Formation", pp. 693–699.

Microcirculation, vol. 6, issued 1999, Feng, D., et al., "Pathways of Macromolecular Extravasation Across Microvascular Endothelium in Response to VPF/VEGF and Other Vasoactive Mediators", pp. 23–44.

Eur. J. Pharmacol., vol. 333, issued 1997, Inoue, H., et al., "Mechanism of mustard oil–induced skin inflammation in mice", pp. 231–240.

Microcirculation, vol. 6, issued 1999, McDonald, D.M., et al., "Endothelial Gaps as Sites for Plasma Leakage in Inflammation", pp. 7–22.

Microcirculation, vol. 6, issued 1999, Michel, C.C. and Neal, C.R., "Openings Through Endothelial Cells Associated with Increased Microvascular Permeability", pp. 45–54.

Nature, vol. 376, issued Jul. 6, 1995, Sato, T.N., et al., "Distinct roles of the receptor tyrosine kinases Tie–2 an Tie–2 in blood vessel formation", pp. 70–74.

Cell, vol. 87, issued Dec. 27, 1996, Suri, C., et al., "Requisite Role of Angiopoietin–1, a Ligand for the TIE2 Receptor, during Embryonic Angiogenesis", pp. 1171–1180.

Science, vol. 282, issued Oct. 16, 1998, Suri, C., et al., "Increased Vascularization in Mice Overexpressing Angiopoietin–1", pp. 468–471.

Am. J. Physiol., vol. 271, issued 1996, Thurston, G., et al., "Permeability–related changes revealed at endothelial cell borders in inflamed venules by lectin binding", pp. H2547–2562.

*Primary Examiner*—Prema Mertz
(74) *Attorney, Agent, or Firm*—Linda O. Palladino; Robert J. Cobert

(57) ABSTRACT

The present invention provides for a method of decreasing or inhibiting vascular permeability and/or plasma leakage in a mammal comprising administering to the mammal a TIE-2 receptor activator. The invention also provides for a method of decreasing or inhibiting vascular permeability and/or plasma leakage in a mammal comprising administering to the mammal an Ang-2 inactivator such as an anti-Ang-2 neutralizing antibody.

2 Claims, 4 Drawing Sheets

Control

K14-Ang1

ANGIOPOIETINS AND METHODS OF USE THEREOF

CROSS-REFERENCE TO RELATED APPLICATIONS

This application claims the benefit of U.S. Provisional Application No. 60/106,539, filed Mar. 26, 1999, which disclosure is herein incorporated by reference.

This invention was made, in part, with U.S. government support under Grant Contract Nos. HL-59157 and HL-24136 awarded by the National Institutes of Health. The government may have certain rights in this invention. Throughout this application various patents and other publications are referenced. The disclosures of each and all of these patents and other publications in their entireties are hereby incorporated by reference into this application.

FIELD OF THE INVENTION

The invention generally relates to angiogenic factors and more particularly to the angiopoietin family of growth factors and to methods of decreasing or inhibiting vascular permeability and/or plasma leakage.

BACKGROUND OF THE INVENTION

Plasma leakage, a key component of inflammation, occurs in a distinct subset of the microvessels. In particular, in most organs plasma leakage occurs specifically in the venules. Unlike arterioles and capillaries, venules become leaky in response to numerous inflammatory mediators including histamine, bradykinin, and serotonin.

One characteristic of inflammation is the plasma leakage that results from intercellular gaps that form in the endothelium of venules. Most experimental models of inflammation indicate that these intercellular gaps occur between the endothelial cells of postcapillary and collecting venules (Baluk, P., et al., Am. J. Pathol. 1998 152:1463–76). It has been shown that certain lectins may be used to reveal features of focal sites of plasma leakage, endothelial gaps, and finger-like processes at endothelial cell borders in inflamed venules (Thurston, G., et al., Am. J. Physiol, 1996, 271: H2547–62). In particular, plant lectins have been used to visualize morphological changes at endothelial cell borders in inflamed venules of, for example, the rat trachea. Lectins, such as conconavalin A and ricin, that bind focally to inflamed venules reveal regions of the subendothelial vessel wall exposed by gaps that correspond to sites of plasma leakage (Thurston, G., et al., Am J Physiol, 1996, 271: H2547–62).

The properties of the microvessels are dynamic. Chronic inflammatory diseases, for example, are associated with microvascular remodeling, including angiogenesis and microvessel enlargement. Microvessels can also remodel by acquiring abnormal phenotypic properties. In a murine model of chronic airway inflammation, we found that airway capillaries acquire properties of venules, including widened vessel diameter, increased immunoreactivity for von Willebrand factor, and increased immunoreactivity for P-selectin. In addition, these remodeled vessels leak in response to inflammatory mediators, whereas vessels in the same position in the airways of normal mice do not.

Certain substances have been shown to decrease or inhibit vascular permeability and/or plasma leakage. For example, mystixins are synthetic peptides that have been reported to inhibit plasma leakage without blocking endothelial gap formation (Baluk, P., et al., J. Pharmacol. Exp. Ther., 1998, 284: 693–9). Also, the beta 2-adrenergic receptor agonist formoterol reduces microvascular leakage by inhibiting endothelial gap formation (Baluk, P. and McDonald, D. M., Am. J. Physiol., 1994, 266:L461–8).

What factors determine whether a vessel will acquire phenotypic features of venules? One apparent clue came from studies of angiopoietin-1 (Ang1), a ligand for the endothelial cell-specific receptor Tie2. In mice that transgenically overexpress Ang1 in the skin under the keratin-14 promoter (K14-Ang1 mice), microvessels in the position of capillaries have widened vessel diameter, immunoreactivity for P-selectin, and immunoreactivity for von Willebrand factor. Thus, these vessels have phenotypic features of venules.

Chronic inflammation is associated with blood vessel formation and enlargement and changes in vessel phenotype. In mice with chronic airway inflammation, strain dependent differences to the same stimulus have been shown to result in either blood vessel proliferation or enlargement, depending on the host response (Thurston, G., et al., Am. J. Pathol., 1998, 153: 1099–112). Analyses of mouse embryos deficient in the TIE-2 receptor illustrate its importance in angiogenesis, particularly for vascular network formation in endothelial cells. Sato, T. N., et al., Nature 376:70–74 (1995). In the mature vascular system, the TIEs could function in endothelial cell survival, maintenance and response to pathogenic influences.

It has been suggested that the TIE receptors play roles in endothelial cell determination, proliferation, differentiation and cell migration and patterning into vascular elements. The predominant expression of the TIE receptors in vascular endothelia suggests that TIE plays a role in the development and maintenance of the vascular system. The TIE receptors are also expressed in primitive hematopoietic stem cells, B cells and a subset of megakaryocytic cells, thus suggesting the role of ligands which bind these receptors in early hematopoiesis, in the differentiation and/or proliferation of B cells, and in the megakaryocytic differentiation pathway. Iwama, et al. Biochem. Biophys. Research Communications 195:301–309 (1993); Hashiyama, et al. Blood 87:93–101 (1996), Batard, et al. Blood 87:2212–2220 (1996).

An angiogenic factor, which was originally called TIE-2 ligand-1 (TL1) but is also referred to as angiopoietin-1 (Ang1), has been identified that signals through the TIE-2 receptor and is essential for normal vascular development in the mouse. By homology screening, an Ang1 relative has been identified and called TIE-2 ligand-2 (TL2) or angiopoietin-2 (Ang2). Ang2 is a naturally occurring antagonist for Ang1 and the TIE2 receptor. For a description of the cloning and sequencing of TL1 (Ang1) and TL2 (Ang2) as well as for methods of making and uses thereof, reference is hereby made to PCT International Publication No. WO 96/11269 published Apr. 18, 1996 and PCT International Publication No. WO 96/31598 published Oct. 10, 1996 both in the name of Regeneron Pharmaceuticals, Inc.; and S. Davis, et al., Cell 87: 1161–1169 (1996) each of which is hereby incorporated by reference. Ang1* is a mutant form of angiopoietin-1 that comprises the N-terminal domain of angiopoietin-2 fused to the coiled-coil domain and the fibrinogen domain of angiopoietin-1 and that has a Cys to Ser mutation at amino acid 245 (See PCT International Publication No. WO 98/05779 published Feb. 12, 1998 in the name of Regeneron Pharmaceuticals, Inc. which is hereby incorporated by reference). Ang1* has been shown to be a potent agonist for the Tie-2 receptor.

Including the above-described angiopoietins, applicants have identified a family of several related angiogenic factors. These have been designated TIE-2 ligand-1 (TL1) also referred to as angiopoietin-1 (Ang1); TIE-2 ligand-2 (TL2) or angiopoietin-2 (Ang2); Tie ligand-3 (TL3) and Tie ligand-4 (TL4). For descriptions of the structure and functional properties of these four related factors, reference is hereby made to the following publications, each of which is hereby incorporated by reference: U.S. Pat. No. 5,643,755, issued Jul. 1, 1997 to Davis, et al.; U.S. Pat. No. 5,521,073, issued May 28, 1996 to Davis, et al.; U.S. Pat. No. 5,650,490, issued Jul. 22, 1997 to Davis, et al.; U.S. Ser. No. 08/348,492, filed Dec. 2, 1994, now allowed, date of allowance Aug. 29, 1997; U.S. Ser. No. 08/418,595, filed Apr. 6, 1995, now allowed, date of allowance Nov. 26, 1996; U.S. Ser. No. 08/665,926, filed Jun. 19, 1996, now allowed, date of allowance Dec. 9, 1997; PCT International Application No. PCT/US95/12935, filed Oct. 6, 1995, published on Apr. 18, 1996, with Publication No. WO 96/11269; and PCT International Application No. PCT/US96/04806, filed Apr. 5, 1996, published on Oct. 10, 1996, with Publication No. WO96/31598, both PCT applications in the name of Regeneron Pharmaceuticals, Inc.

The angiopoietins can be structurally divided into three domains: an N terminal region lacking in homology to any known structures; an alpha-helical rich coil-coil segment similar to motifs found in many proteins that seem to promote multimerization; and a "fibrinogen-like domain" thus dubbed because it is distantly related to a domain first found in fibrinogen but now noted to be in many other proteins (Davis, S. et al., (1996) Cell 87: 1161–1169). The fibrinogen-like domain represents the most conserved region of the angiopoietins, and recent studies indicate that it comprises the receptor-binding portion of an angiopoietin. In addition, all the information that determines whether an angiopoietin is an agonist or an antagonist appears to reside within the fibrinogen-like domain. For example, when chimeric molecules are made in which the fibrinogen-like domains of angiopoietin-1 and angiopoietin-2 are swapped, agonistic or antagonistic abilities track with the fibrinogen-like domains. The N-terminal and coil-coil regions appear to serve mainly to multimerize the fibrinogen-like domains, which apparently must be clustered to be active. In fact, the N-terminal and coil-coil regions can be substituted for by alternative motifs that allow clustering. Thus, the activities of angiopoietin-1and angiopoietin-2 can be precisely mimicked by surrogates in which the fibrinogen-like domains (FD) of these factors are fused to the constant region of an antibody, resulting in FD-Fc fusions, which can then be clustered using secondary antibodies directed against the Fc. For example, TIE-2 ligand 1 contains a "coiled coil" domain and a fibrinogen-like domain. The fibrinogen-like domain of TIE-2 ligand 2 is believed to begin on or around the same amino acid sequence as in ligand 1 (FRDCA). The fibrinogen-like domain of TIE ligand-3 is believed to begin on or around the amino acid sequence which is encoded by nucleotides beginning around position 929 as set forth in FIGS. 6A–6B in International Publication No. WO 97/48804 published Dec. 24, 1997. Multimerization of the coiled coil domains during production of the ligand hampers purification. As described in Example 7 of International Publication No. WO 97/48804, Applicants have discovered, however, that the fibrinogen-like domain comprises the TIE-2 receptor binding domain. The monomeric forms of the fibrinogen-like domain do not, however, appear to bind the receptor. Studies utilizing myc-tagged fibrinogen like domain, which has been "clustered" using anti-myc antibodies, do bind the TIE-2 receptor. [Methods of production of "clustered ligands and ligandbodies are described in Davis, et al. Science 266:816–819 (1994)]. Based on these finding, Applicants produced "ligandbodies" which comprise the fibrinogen-like domain of the TLE-2 ligands coupled to the Fc domain of IgG ("fFc's"). These ligandbodies, which form dimers, efficiently bind the TIE-2 receptor. Accordingly, the present invention contemplates the production of TIE ligand-3 or TIE ligand-4 ligandbodies which may be used as targeting agents, in diagnostics or in therapeutic applications, such as targeting agents for tumors and/or associated vasculature wherein a TIE antagonist is indicated.

In order to test whether the fibrinogen-like domain (F-domain) of the TIE-2 ligands contained TIE-2 activating activity, expression plasmids were constructed which deleted the coiled-coil domain, leaving only that portion of the DNA sequence encoding the F-domain (beginning at about nucleotide 1159, amino acid residue ARG284) This mutant construct was transiently transfected into COS cells. The supernatant containing the recombinant protein was harvested. The TL1/F-domain mutant was tested for its ability to bind the TIE-2 receptor. The results showed that, as a monomer, the TL1/F domain mutant was not able to bind TIE-2 at a detectable level. However, when the TL1/F-domain monomer was myc-tagged and subsequently clustered with an antibody directed against the myc tag, it did exhibit detectable binding to TIE-2 However, the antibody clustered TL1/F-domain mutant was not able to induce phosphorylation in a TIE-2 expressing cell line. FIG. 3 of International Publication No. WO 97/48804 shows a schematic representation of the F-domain construct and its binding ability plus and minus antibody clustering. For a general description of the production and use of FD-Fc fusions, see International Publication Number WO 97/48804 published Dec. 24, 1997. Using these techniques, one of skill in the art would be able to similarly make FD Fc fusions using the fibrinogen-like domain of an Angiopoietin family member. One practical advantage of such surrogates is that native angiopoietins can be difficult to produce recombinantly, while the surrogates can be more easily produced.

The absence of Ang1 causes severe vascular abnormalities in the developing mouse embryo (C. Suri, et al., Cell, 1996, 87: 1171–1180). Ang1 and Ang2 have been described as naturally occurring positive and negative regulators of angiogenesis. Positive or negative regulation of TIE2 is likely to result in different outcomes depending on the combination of simultaneously acting angiogenic signals.

The angiopoietins and members of the vascular endothelial growth factor (VEGF) family are the only growth factors thought to be largely specific for vascular endothelial cells. Targeted gene inactivation studies in mice have shown that VEGF is necessary for the early stages of vascular development and that Ang-1 is required for later stages of vascular remodeling. It has been reported that transgenic overexpression of Ang-1 in the skin of mice produces larger, more numerous, and more highly branched vessels, however the characteristics of the resultant vessels are largely unknown (Suri, C., et al., Science, 1998, 282:468–171). The present invention is the result of applicants'efforts to examine these vessels in greater detail by, among other studies, assaying for vessel permeability/plasma leakage.

SUMMARY OF THE INVENTION

The present invention provides for a method of decreasing or inhibiting vascular permeability and/or plasma leakage in a mammal comprising administering to the mammal a TIE-2 receptor activator. By way of example, but not by way of limitation, the vascular permeability/plasma leakage may be produced by an inflammatory agent or by injury. In one embodiment of the invention, the mammal is a human. By vascular permeability, what is meant is any process that leads to leakage or extravasation of plasma. including, but not limited to, increased endothelial permeability. See for example, McDonald, D. M., et al., Microcirculation 6: 7–22 (1999); Feng, D., et al., Microcirculation 6: 23–44 (1999); and Michel, C. C., and Neal, C. R., Microcirculation 6: 45–54 (1999) each of which is incorporated by reference herein in its entirety.

The invention further provides for a method wherein the TIE-2 receptor activator is Angiopoietin-1, or a fragment or derivative thereof capable of activating the TIE-2 receptor.

The invention also provides for a method wherein the TIE-2 receptor activator is an activating antibody, or a fragment or derivative thereof capable of activating the TIE-2 receptor.

The invention further provides for a method wherein the TIE-2 receptor activator is a small molecule, or a fragment or derivative thereof capable of activating the TIE-2 receptor.

The invention also provides for a method of decreasing or inhibiting vascular permeability and/or plasma leakage in a mammal comprising administering to the mammal an Ang-2 inactivator such as an anti-Ang-2 neutralizing antibody. In one embodiment of this invention, the mammal is a human. The invention also provides for a method wherein the anti-Ang-2 neutralizing antibody is a monoclonal antibody. The invention further provides for a method wherein the anti-Ang-2 neutralizing antibody is a polyclonal antiserum. Alternatively the Ang-2 inactivator could be a small molecule.

The invention also provides for a composition comprising an Ang-2 inactivator in a vehicle, as well as a method of regulating angiogenesis in a patient comprising administering to the patient an effective amount of the composition. In one embodiment, the Ang-2 inactivator is a small molecule. The invention also provides for a composition comprising an anti-Ang-2 neutralizing antibody in a vehicle, as well as a method of regulating angiogenesis in a patient comprising administering to the patient an effective amount of the composition.

DETAILED DESCRIPTION OF THE INVENTION

Figure 1:
FIG. 1—Ricin Stain Showing Vessels in Ang-1 Overexpressing Mice are resistant to Mustard Oil Induced Vascular Leakage—The microvasculature of mice overexpressing angiopoietin-1 in the skin (K14-Ang1—bottom panel) and wild-type control FVB/N mice (control—top panel) was stained by perfusion of fluorescent lectin (ricin) and immersion in antibodies to P-selectin or von Willebrand factor, then examined in whole mounts of the ear skin.
Figure 1:

As described in greater detail below, applicants have invented a method of decreasing or inhibiting vascular permeability and/or plasma leakage in a mammal comprising administering to the mammal a TIE-2 receptor activator. By way of example, but not by way of limitation, the vascular permeability/plasma leakage may be produced by an inflammatory agent or by injury. In one embodiment of the invention, the mammal is a human.

The invention further provides for a method wherein the TIE-2 receptor activator is Angiopoietin-1, or a fragment or derivative thereof capable of activating the TIE-2 receptor.

The invention also provides for a method wherein the TIE-2 receptor activator is an activating antibody, or a fragment or derivative thereof capable of activating the TIE-2 receptor.

The invention further provides for a method wherein the TIE-2 receptor activator is a small molecule, or a fragment or derivative thereof capable of activating the TIE-2 receptor.

The invention also provides for a method of decreasing or inhibiting vascular permeability and/or plasma leakage in a mammal comprising administering to the mammal an Ang-2 inactivator such as an anti-Ang-2 neutralizing antibody. In one embodiment of this invention, the mammal is a human. The invention also provides for a method wherein the anti-Ang-2 neutralizing antibody is a monoclonal antibody. The invention further provides for a method wherein the anti-Ang-2 neutralizing antibody is a polyclonal antiserum. Alternatively the Ang-2 inactivator could be a small molecule.

The invention also provides for a composition comprising an Ang-2 inactivator in a vehicle, as well as a method of regulating angiogenesis in a patient comprising administering to the patient an effective amount of the composition. In one embodiment, the Ang-2 inactivator is a small molecule. The invention also provides for a composition comprising an anti-Ang-2 neutralizing antibody in a vehicle, as well as a method of regulating angiogenesis in a patient comprising administering to the patient an effective amount of the composition.

By way of example, but not limitation, the method of the invention may be useful in treating clinical conditions that are characterized by plasma leakage/vascular permeability, edema or inflammation such as brain edema associated with injury, stroke or tumor; edema associated with inflammatory disorders such as psoriasis or arthritis, including rheumatoid arthritis; asthma; generalized edema associated with burns; ascites and pleural effusion associated with tumors, inflammation or trauma; chronic airway inflammation; capillary leak syndrome; sepsis; kidney disease associated with increased leakage of protein; and eye disorders such as age related macular degeneration and diabetic retinopathy.

The compositions of the invention may be administered systemically or locally. Any appropriate mode of administration known in the art may be used, including, but not limited to, intravenous, intrathecal, intraarterial, intranasal, oral, subcutaneous, intraperitoneal, or by local injection or surgical implant. Sustained release formulations are also provided for.

For preparation of monoclonal antibodies, any technique which provides for the production of antibody molecules by continuous cell lines in culture may be used. For example, the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in "Monoclonal Antibodies and Cancer Therapy," Alan R. Liss, Inc. pp. 77–96) and the like are within the scope of the present invention.

The monoclonal antibodies may be human monoclonal antibodies or chimeric human-mouse (or other species) monoclonal antibodies. Human monoclonal antibodies may be made by any of numerous techniques known in the art (e.g., Teng et al., 1983, Proc. Natl. Acad. Sci. U.S.A. 80:7308–7312; Kozbor et al., 1983, Immunology Today 4:72–79; Olsson et al., 1982, Meth. Enzymol. 92:3–16). Chimeric antibody molecules may be prepared containing a mouse antigen-binding domain with human constant regions (Morrison et al., 1984, Proc. Natl. Acad. Sci. U.S.A. 81:6851, Takeda et al., 1985, Nature 314:452).

Various procedures known in the art may be used for the production of polyclonal antibodies. For the production of Ang-2 inactivating antibodies, various host animals, including but not limited to rabbits, mice and rats can be immunized by injection with Ang-2, or a fragment or derivative thereof. For the production of TIE-2 activating antibodies, various host animals, including but not limited to rabbits, mice and rats can be immunized by injection with TIE-2 receptor extracellular domain, or a fragment or derivative thereof. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*.

A molecular clone of an antibody to a selected epitope can be prepared by known techniques. Recombinant DNA methodology (see e.g., Maniatis et al., 1982, Molecular Cloning, A Laboratory Manual, Cold Spring Harbor Laboratory, Cold Spring Harbor, N.Y.) may be used to construct nucleic acid sequences which encode a monoclonal antibody molecule, or antigen binding region thereof.

The present invention provides for antibody molecules as well as fragments of such antibody molecules. Antibody fragments which contain the idiotype of the molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent. Antibody molecules may be purified by known techniques, e.g., immunoabsorption or immunoaffinity chromatography, chromatographic methods such as HPLC (high performance liquid chromatography), or a combination thereof.

EXAMPLES

It was previously shown that transgenic overexpression of Ang-1 in the skin of mice (K14-Ang1) as described by Suri, C., et al., 1998, Science 282: 468–471, hereby incorporated by reference in its entirety, produces larger, more numerous, and more highly branched vessels.

The microvasculature of mice overexpressing angiopoietin-1 in the skin (K14-Ang1) and wild-type control FVB/N mice was then stained by perfusion of fluorescent lectin and immersion in antibodies to P-selectin or von Willebrand factor, as generally described in Thurston, G. et al., 1998, Am. J. Pathol. 153(4):1099–112, hereby incorporated by reference in its entirety, then examined in whole mounts of the ear skin as shown in FIG. 1.

Plasma leakage from ear vessels was measured in some mice after topical application of the inflammatory agents mustard oil or serotonin (See Inoue, H, et al., 1997, Eur. J. Pharmacol. 333:231–40) with the tracer Evans blue (See Baluk, P., et al., 1997, Am. J. Physiol. 272:L155–170). Plasma leakage was measured using the tracer dye Evans blue. Evans blue (EM Sciences, Cherry Hill, N.J.) 30 mg/kg in a volume of 100 μl was injected into one femoral vein of anesthetized mice, and 1 min later mustard oil or serotonin was administered to one ear. Mustard oil (Sigma, St. Louis, Mo.) was diluted to 5% in mineral oil and applied with a Q-tip to the dorsal and ventral surfaces of the skin of one ear, and nothing was done to the other ear (baseline control). Serotonin (Sigma) was made up at 0.22 mg/ml in sterile saline plus 0.005 N acetic acid (vehicle). Approximately 10 μl was injected intradermally into the dorsal ear skin, and a similar volume of vehicle was injected into the other ear (control). Thirty minutes after the stimulus, the vasculature was perfusion fixed (1% paraformaldehyde in 50 mM citrate buffer, pH 3.5) for 2 min. Ears were removed, blotted dry, and weighed. Evans blue was extracted from the ears with formamide and measured with a spectrophotometer at 610 nm.

We found vessels in the position of capillaries in the skin of K14-Ang1 mice were abnormally large and had phenotypic properties of venules, including strong immunoreactivity for P-selectin and von Willebrand factor. By comparison, in wild type mice the immunoreactivity of these proteins was largely restricted to venules. The microvasculature of ear skin was not leaky in either group of mice under baseline conditions (6.7±1.7 ng of Evans blue per mg wet tissue weight in K14-Ang1 mice compared to 6.4±1.6 ng/mg in wild-type mice), but was significantly less leaky in K14-Ang1 mice compared to control after treatment with mustard oil (5.9±1.8 ng/mg in K14-Ang1 vs 18.1±3.9 ng/mg in wild-type mice)—See FIG. 2, top panel. Vessels in K14-Ang1 mice were also resistant to leakage after treatment with serotonin—See FIG. 2, bottom panel. Although overexpression of angiopoietin-1 induced some of the phenotypic features of venules, skin vessels in K14-Ang1 mice are more resistant to leakage induced by inflammatory stimuli.

Figure 2:
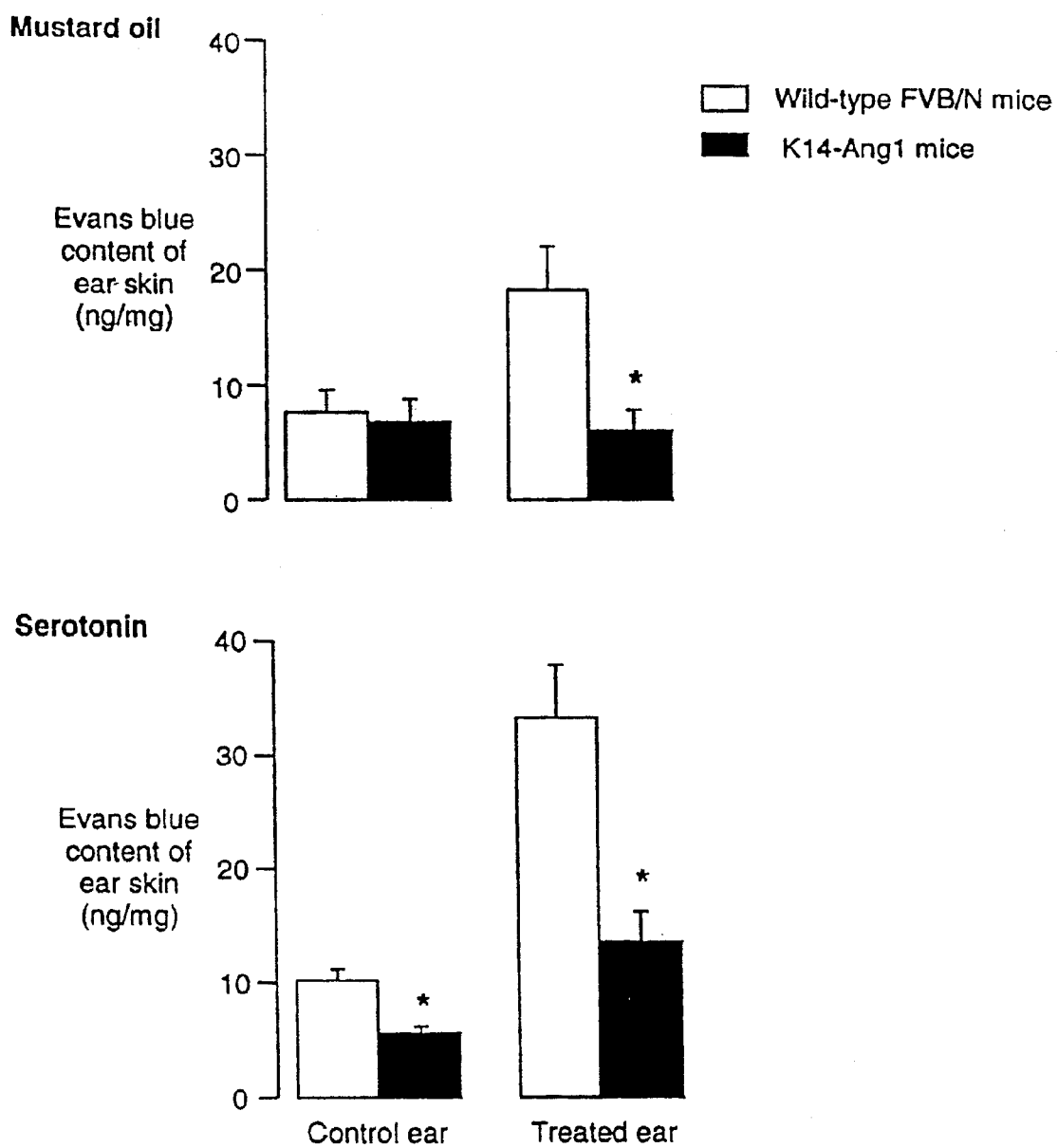
FIG. 2—Leakage From Ear Vessels of Wild-Type and K14-Ang-1 Mice —Mustard oil (5%) was applied to surface of ear skin, control ear received no treatment. Serotonin (10 µg/ml) was injected dermally, control ear received injection of vehicle. Leakage was measured at 30 min after stimulus, n=4 to 6 ears per group, values are mean±SE. *Significantly different from corresponding wild=type value, P<0.05, Bonferroni/Dunn test.

In summary, we found that the inflammatory mediator mustard oil induced plasma leakage in the ear skin of wild-type mice. However, contrary to our expectations, we found that mustard oil did not induce significant leakage in K14-Ang1 transgenic mice (FIG. 2). Furthermore, we found that another inflammatory mediator, serotonin, also failed to induce significant leakage in K14-Ang1 mice (FIG. 2).

Figure 3:
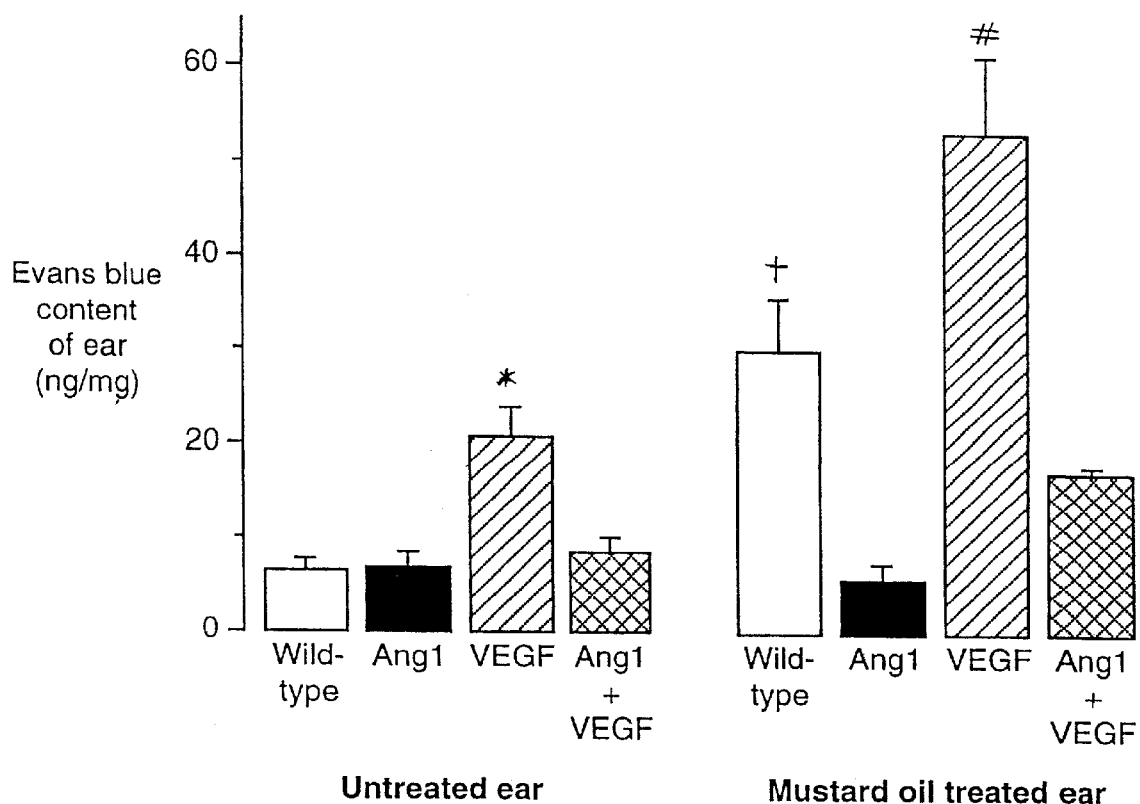
FIG. 3—Amount of extravasation of Evans blue in ears of wild-type, K14-Ang1, K14-VEGF, and K14-Ang1/VEGF mice 30 minutes after topical application of mustard oil. Asterisk marks significantly greater leakage in untreated ears of K14-VEGF mice than in untreated ears of wild-type, K14-Ang1, or K14-Ang1/VEGF mice. Cross marks significantly greater leakage in treated ears of wild-type mice than in treated ears of K14-Ang1 or K14-Ang1/VEGF mice. # marks significantly greater leakage in treated ears of K14-VEGF mice than in treated ears of K14-Ang1 or K14-Ang1/VEGF mice.

In another set of experiments, we found that skin vessels in mice that overexpress VEGF have increased baseline leakage. The vessels in these mice showed further increases in leakage after stimulation with mustard oil. However, unexpectedly, the high baseline leakage in K14-VEGF transgenic mice was reduced to normal values in double transgenic K14-VEGF/Ang1 mice (FIG. 3). In addition, mustard oil did not induce significant leakage in double transgenic K14-VEGF/Ang1 mice (FIG. 3). These experiments establish that transgenic overexpression of angiopoietin-1 results in vessels that are resistant to leakage induced by inflammatory mediators (mustard oil, serotonin) and by transgenic overexpression of VEGF.

Figure 4:
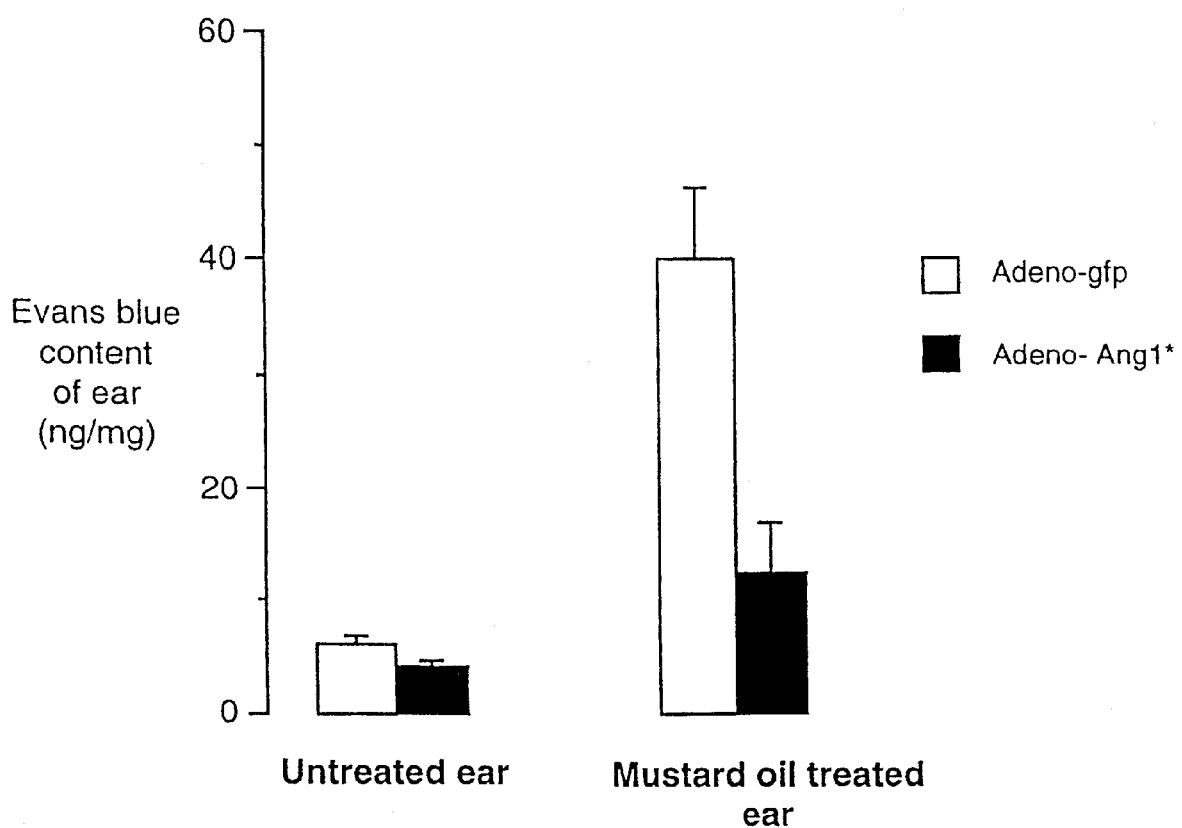
FIG. 4—Amount of extravasation of Evans blue in ears of wild-type mice injected intravenously with adenovirus expressing Angiopoietin-1* or adenovirus expressing green fluorescent protein six days earlier, and then treated for 30 minutes by topical application of mustard oil.

To determine whether acute administration of angiopoietin-1 can also reduce inflammation-associated leakage, we used an adenovirus encoding for angiopoietin-1* (adeno-Ang1*) to produce high systemic levels in otherwise normal mice. Angiopoietin-1* has been shown to be a potent agonist for the Tie-2 receptor. Plasma leakage was tested in ear skin of mice given this virus by iv injection. Control mice received iv injection of adenovirus encoding for a non-active protein (green fluorescent protein—GFP). At 6 days after administration of adenovirus, the amount of plasma leakage induced by mustard oil was significantly less in mice given adeno-Ang1* than in those given adeno-GFP (FIG. 4). This experiment establishes that administration of angiopoietin-1 to wild-type mice can result in vessels that are resistant to inflammation-induced leak.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

What is claimed is:

1. A method of decreasing or inhibiting plasma leakage in a mammal comprising administering to the mammal a TIE-2 receptor activator, wherein the TIE-2 receptor activator is Angiopoietin-1, Ang1*, or a fragment thereof capable of activating the TIE-2 receptor.

2. The method of claim 1, wherein the mammal is a human.

* * * * *

UNITED STATES PATENT AND TRADEMARK OFFICE
CERTIFICATE OF CORRECTION

PATENT NO.    : 6,455,035 B1
DATED         : September 24, 2002
INVENTOR(S)   : Citra Suri et al.

It is certified that error appears in the above-identified patent and that said Letters Patent is hereby corrected as shown below:

<u>Title page,</u>
Item [73], Assignee, please correct the Assignee information as follows: -- Regeneron Pharmaceuticals, Inc. Tarrytown, NY and The Regents of the University of California Oakland, CA --

Signed and Sealed this

Nineteenth Day of August, 2003

JAMES E. ROGAN
*Director of the United States Patent and Trademark Office*